United States Patent [19]

Head

[11] Patent Number: 4,833,413
[45] Date of Patent: May 23, 1989

[54] SALINITY MEASURING SYSTEM

[76] Inventor: Michael J. Head, 699 N. Vulcan, #88, Encinitas, Calif. 92024

[21] Appl. No.: 177,373

[22] Filed: Apr. 1, 1988

[51] Int. Cl.⁴ .................... G01N 27/06; G01N 27/07
[52] U.S. Cl. .................... 324/449; 324/444; 324/446; 324/450
[58] Field of Search ............... 324/439, 444, 446, 449, 324/450, 65 P

[56] References Cited

U.S. PATENT DOCUMENTS

| | | | |
|---|---|---|---|
| 3,474,330 | 10/1969 | Dauplinee | 324/444 |
| 4,137,495 | 1/1979 | Brown | 324/450 |
| 4,365,200 | 12/1982 | Goldsmith | 324/444 |
| 4,591,793 | 5/1986 | Freilich | 324/446 |

*Primary Examiner*—Reinhard J. Eisenzopf
*Assistant Examiner*—Anthony L. Miele
*Attorney, Agent, or Firm*—Ralph S. Branscomb

[57] ABSTRACT

A salinity measuring apparatus utilizes a specialized probe with dual electrode pairs, one of the pairs being used to pass current through the electrolyte, while the other picks up voltage drop across a region in the electrolyte and feeds it back to the current producing amplifier, which adjusts the current output until a stabilized, predetermined voltage difference occurs across the voltage electrodes. The circuit which drives the current between the current electrodes produces a positive pulse, and an ensuing negative pulse, which are sequentially applied across the electrodes so that two separate measurements are made using pulses of opposite polarity to cancel out electrode polarizations. An amplifier circuit receives a pulse from the voltage source and applies it to the electrodes. A second amplifier circuit picks up a voltage across a voltage dropping resister in series with the resistance of the electrolyte between the current electrodes, and amplifies this voltage drop for outputting to a signal register and processing means. A polarity reversal system is used at the output of the second amplifying circuit so that all of the processed pulses which output from the system have the same polarity despite the fact that internally in the apparatus the polarity is reversed. The pulse is transferred to the first amplifier circuit by a capacity charged transfer technique so that the system is electrically isolated from the pulse generator, and a second capacity transfer at the system output isolates the system from the output signal register and processing device.

7 Claims, 2 Drawing Sheets

SALINITY MEASURING SYSTEM

BACKGROUND OF THE INVENTION

This invention relates to the measurement of the salinity of water, and particularly to the measurement of salinity using an electrical conductivity or resistance measuring system.

The electrical conductivity of sea water is related to the concentration of salt ions in the water and can be derived with considerable accuracy when the temperature of the water is known. Much effort has been spent establishing formulas that relate electrical conductivity, temperature, and ionic concentration. Since salt concentration, in the absence of mixing, is a conservative property away from the ocean's surface, it may be used to identify water masses in the oceans, and to track their motions. This is true both for large global scale motions that occur very slowly in time, and also for small scale motions that result in slight vertical mixing.

The investigation of large scale motions requires measurements of high accuracy if data from widely different times or places are to be compared. Investigation of small scale mixing processes requires high spacial resolution since mixing results from molecular diffusion over very small distances. For practical measurement of both types of motions it is valuable to have a measurement system which is capable of rapid measurement, is small, and can be battery operated in locations remote from an external power supply.

There are currently in use conductivity measuring systems which cause current to flow through the electrolyte either by induction or conduction. Inductive devices, while being highly stable, suffer from poor spacial resolution. On the other hand, conductive devices are capable of high spacial resolution but are often unstable due to changes in electrode polarization or electrode fouling. In these devices, electrode polarization effects are often reduced by making a four-electrode measurement and also by placing non-conducting barriers near the electrodes to increase the electrical current density thereby increasing the solution resistance relative to the electrode polarization. Electrode fouling effects are reduced by locating the voltage electrodes in areas of low current density.

Two patents relating to a salinity measuring system utilizing four electrodes are issued to Thomas M. Dauphinee, et al. in U.S. Pat. Nos. 3,963,979, issued on June 15, 1976, and 4,511,845, issued on Apr. 16, 1985. Both of these systems comprise laboratory based, relatively elaborate systems in which a glass tube containing specimen salt water is immersed in a temperature controlled bath. The four electrodes contact the solution in the specimen tube, and the salinity of the solution is measured by the application of a continuous square wave pulse train to the saline solution to create a current and then measuring the voltage drop caused by that current in a manner somewhat analogous to that of the instant application.

Another prior art device is disclosed in U.S. Pat. No. 3,939,408, issued Feb. 17, 1976, to Neil L. Brown. This patent is also somewhat analogous both the above-referenced systems and the instant system, and sets forth a T-shaped probe with a very particular arrangement of electrodes, for immersion and current production in a saline solution.

There is a need for a portable system for measuring salinity, which is small and lightweight, and which is designed to inhibit polarization and electrode fouling, uses a minimum amount of current, and produces a very accurate measurement.

SUMMARY OF THE INVENTION

The disclosed apparatus fulfills the above-stated need by providing a portable, high resolution, battery operated, ground-independent system with built-in features minimizing polarization and electrode fouling and maximizing accuracy and battery life.

The apparatus has a specialized probe consisting of a strip of substrate material with two electrodes on each face of the substrate near one end. A cylinder surrounding that one end creates the desirable current density inside the cylinder, and the spacial arrangement of the electrodes removes the voltage electrodes slightly from the main current flow, so that they are even less susceptible to fouling.

The electronic system of the invention utilizes a pulse generation system which produces pulses of alternately opposite polarity. The opposite polarity of successive pulses helps neutralize errors and electrode polarizations. A pulse train of only two pulses of opposite polarity is all that is needed to produce a reading, although pulse trains of up to 100 pulse pairs may be used to provide even further accuracy.

A voltage from the battery voltage source charges a first capacitor, which is subsequently disconnected from the source and connected to the first amplifier circuit. This circuit produces a current through the current electrodes of the probe, and senses voltage drop at the voltage electrodes, and with the feedback from the voltage electrodes adjusts the current through the current electrodes as necessary until the voltage across the voltage electrodes is stabilized.

A voltage dropping resister in series with the resistance of the saline solution provides a potential difference drop for a second amplifier circuit, which is amplified and subsequently output through a capacitor transfer system similar to the one described above, to an external circuit which is not part of this patent application. The output of each pulse is converted to a digital integer format by an analog to digital converter. The result from the +pulse is added to the result from the -pulse and the sum divided by two.

DETAILED DESCRIPTION OF THE PREFERRED EMBODIMENT

Figure 1:
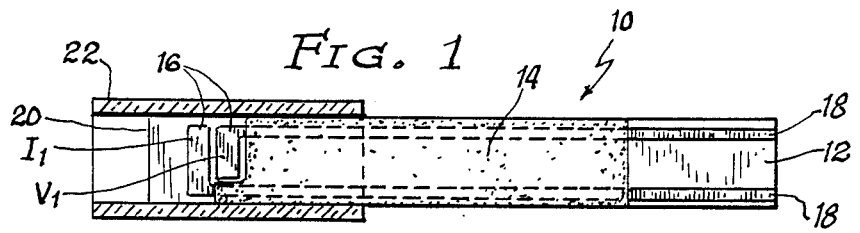
FIG. 1 is a section taken through the probe illustrating the top of the insulating substrate and two electrodes.
Figure 2:
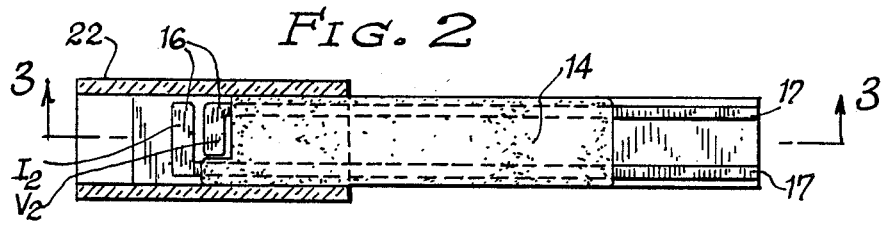
FIG. 2 is a similar view to FIG. 1, but of the opposite side of the probe.

Referring to FIGS. 1 through 4, the conductivity cell or probe 10 comprises a rectangular strip 12 of substrate material. The substrate strip is preferably made of a ceramic material, and in the production model measures 0.190 inches wide, 1.3 inches long, and 0.025 inches thick.

On the opposite sides of the substrate are electrodes I-1, V-1 and I-2, V-2, respectively. These electrodes are applied by depositing a thick film of a platinum composition to the substrate with a screening process, and firing it into place. An insulator 14 of a glass material in fired in place over the electrodes, leaving only the tips 16 exposed. The lead-ins 18 of the deposited electrodes are easily soldered to connectors, with everything except the exposed tips 16 being well-insulated.

Figures 3, 4:
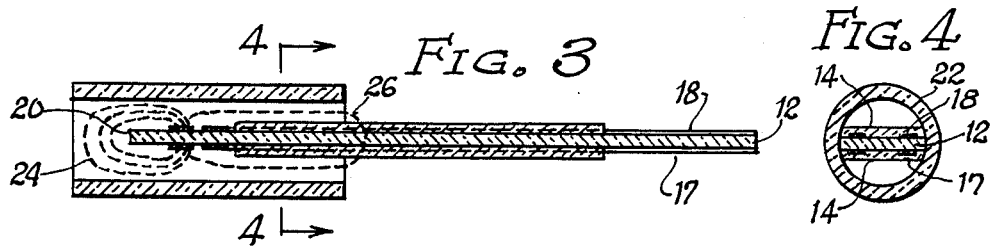
FIG. 3 is a section taken along line 3—3 of FIG. 2.
FIG. 4 is a section taken along line 4—4 of FIG. 3.

At one end 20 of the substrate 12, the substrate strip is bonded along its edges to the inside of a sheath 22, which is shown in FIG. 4 as being a cylinder, but which could also be square, or some other cross sectional shape. This sheath is open at both ends to permit the circulation of sea water, and as shown in FIG. 3, it defines a certain current density in the sea water, in as much as it is an insulator. The current from the current electrodes I-1 and I-2 follows a path 24 over the end 20 of the substrate. A very minor current path 26 also exists, which does not interfere with the accuracy and effectiveness of the probe.

The geometry of the probe, with the cylindrical sheath, not only concentrates the current in the current path 24, but also results in the removal of the voltage electrodes V-1 and V-2 slightly from the main current path. Because the voltage electrodes are placed in regions of relatively low current density the overall measurement is less sensitive to polarization and fouling of the electrodes.

The entire device which constitutes the present invention is encapsulated in a cylinder about three feet long. The cylinder contains the circuitry, the probe, which is of course exposed to sea water, and batteries for operation, so that it is entirely self-contained.

Figure 5:
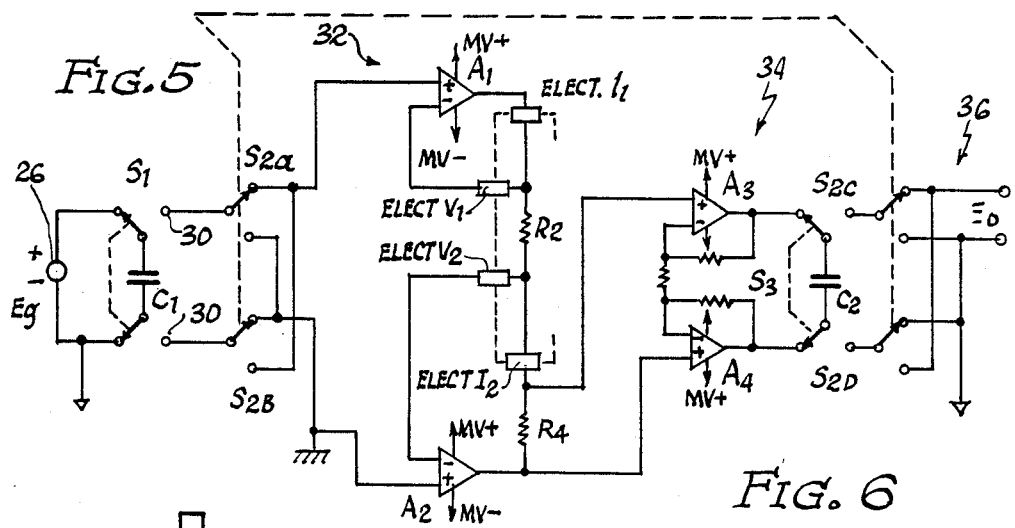
FIG. 5 is a schematic diagram of the basic circuit.

The theory that the circuitry of the invention operates on is as follows: Referring to FIG. 5, a DC battery voltage source supplies a voltage to capacitor C-1. This voltage source is described in more detail below. The charged capacitor C-1 sources voltage to the first amplifier circuit 32 when the switch S-1 is closed, making contact with contacts 30. Capacitor C-1 provides a voltage to the amplifier circuit through switch S-2.

The amplifiers 32 produce current through the current electrodes. This current flows through the electrodes, and through the resistance R-2, which represents resistance of the sea water that the system is sampling. In series with the sea water resistance R-2 is provided a resistor R-4, which is a voltage drop resistor which provides a voltage for subsequent circuitry which is proportional to the current through the saline solution R-2.

Electrodes V-1 and V-2 feed back the voltage drop in the current cell to the amplifiers A-1 and A-2. Amplifiers A-1 and A-2, comprising the active part of the first amplifier circuit 32, adjust the output current that they produce in response to the voltage feedback they receive from electrodes V-1 and V-2, so that the current output rises or falls to the level necessary to produce a predetermined voltage drop across the voltage electrodes, that is stable over a short period of time within the duration of the pulse. This circuit arrangement causes the voltage across R-2 to be stabilized against changes in surface impedance of the four electrodes.

The voltage drop across the voltage electrodes is maintained at the same level independent of the solution in which the cell is immersed. Current through the resistor R-2 is adjusted until that voltage drop is achieved. The magnitude of the current is then correlated with the conductance or resistance of the saline solution. A very low salinity, for example, would cause a high resistance and thus a small amount of current to produce a standard voltage drop, whereas a very saline solution would produce a very low resistance which would require a high current to cause the predetermined voltage drop between the voltage electrodes.

Thus, the voltage drop across resister R-4 is directly correlated with the salinity of the sample solution. This voltage is applied across the second amplifier circuit 34 consisting of amplifiers A-3 and A-4, which apply the voltage as modified by their action to capacitor C-2. This capacitor is being charged up while capacitor C-1 is supplying a fixed voltage to the amplifier circuit 32, and at approximately the moment at which switch S-1 separates capacitor C-1 from the amplifier circuit, switch S-3 moves from the position shown in FIG. 6 to the output position in which the output circuitry 36 is charged. This output circuitry delivers the voltage of capacitor C-2 to a circuit which measures and preserves the signal magnitude, which is not part of this invention.

When the probe is immersed in a solution, the circuit as described will produce a voltage level output which is converted to a digital read-out by the output circuitry, not described. Calibration of the instrument is achieved empirically for the most part, by inserting the probe in samples of known salinity (or conductivity) and noting the reading, and then interpolating between the read-out points.

The use of the capacitors C-1 and C-2 to transfer a voltage charge from the source, and then from the amplifier circuits to the output, cause the electrical isolation of the main circuitry from ambient ground. This is necessary for great accuracy as it eliminates the effect of trace currents and voltages in the system environment.

The above states the general theory under which the system works. However, this simple theory is modified somewhat by the actual use of two consecutive pulses of opposite polarity to probe the sea water. Reversing of the polarity of the sequential pulses is achieved by switches S-2a and S-2b. As can be seen in FIG. 5, the only result of throwing these switches is the reversal of the polarity of the signal as delivered to the amplifier circuit 32. The reversed polarity pulse has the effect of reversing the electrode polarizations and signal inaccuracies of the system so they cancel out their counterparts in the positive signal.

At the output however, it is desirable to have a signal of a single polarity, so to this extent, switches S-2c and S-2d again reverse the polarity, in this example back to positive. The output circuitry thus receives two sequential positive signals, which converts them to digital integers and averages them together.

Figure 6:
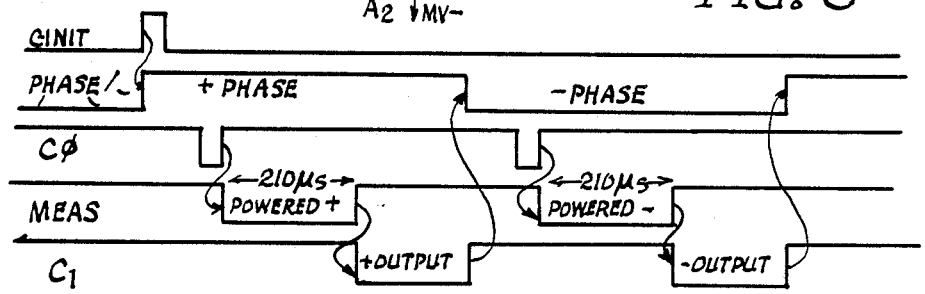
FIG. 6 is a diagram of the various pulse forms in the control circuitry.
Figure 7:
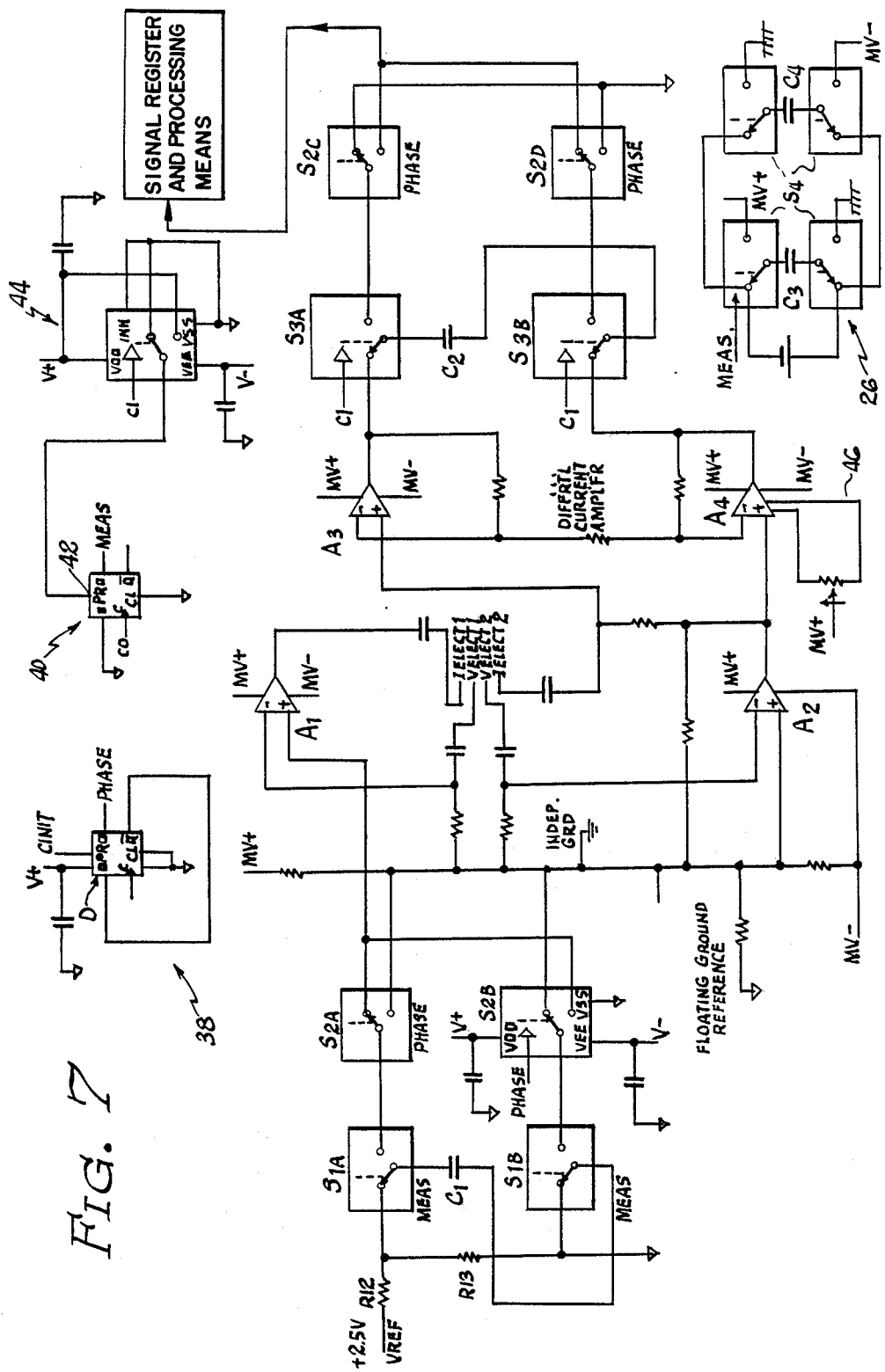
FIG. 7 is a more detailed schematic diagram.

A more detailed illustration of the circuit is provided in FIG. 7, particularly relating to the switching of the circuit and how it is sequenced. The pulse wave form diagram controlling the sequencing is shown in FIG. 6.

The system operates on three clock signals from a source which is not shown. These three sources are designated C-INIT, for initiating clock, and C-0 and C-1. The pulse forms of these inputs are illustrated in FIG. 6. Also, the curved arrows connecting the various edges of these pulses to the phase signal and the "MEAS" indicate how the input clock signals generate two other pulse signals which control most of the switches in the circuit.

Turning to the "PHASE" pulse, the "D" flip-flop 38 receives the C-INIT input and the C-1 signal. Data input is tied to Q Neg., so that the Q output which produces the "PHASE" signal is initially set high by C-INIT, and subsequently has a toggle action at the positive leading edge of the C-1 input to produce the alternate "+PHASE" and "−PHASE" pulses indicated in FIG. 6.

The PHASE pulse controls switches S-2a through S-2d, as indicated at switch S-2b. During the opposite polarities of the phase input, the switch is connected to opposite poles.

The other "D" flip-flop 40 has a similar action, with the data input tied to ground and the active low preset 42 producing alternate high and low states from the switch 44 which is driven by the clock input C-1.

The output "MEAS" signal is clocked low by the positive edge of the C-0 input signal because the data input is tied to ground, and the negative edge of the C-1 pulse from the delay line and invertor 44 raises the "MEAS" pulse to a high again, as illustrated in FIG. 6. The "MEAS" pulse rise lags slightly behind the C-1 clock pulse because of the delay line 44 to insure that the C-1 capacitor is not switched out of the circuit before the C-2 capacitor is switched to output. If this were permitted to happen, voltage levels in the circuit would immediately start dissipating with the withdrawal of C-1, before C-2 would be removed from the circuit, taking its accurate charge with it to the output.

This sequencing controls the switches as follows, with reference to FIG. 7. Clearly, clock inputs C-0 and C-1 are on the same cycle. When the "MEAS" signal is low, this actuating pulse throws switches S-1a and S-1b, transferring the charge which has accumulated on capacitor C-1 from the 2.5 volt positive reference to the amplifier side of the circuit.

As indicated in FIG. 6, the first time this occurs switches S-2a through S-2b are in their positive phase cycle, corresponding to the positive voltage that is received from the source. Thus, a positive pulse is introduced and processed through the two amplifier circuits.

When the positive pulse terminates at the occurrence of the negative edge of the C-1 clock pulse, at the same time, switches S-3a and S-3b which are directly controlled by the C-1 clock pulse switch the capacitor C-2 from its previous connection to the two amplifier circuits, where is was charged to a voltage proportional to current flowing in R-2, to the output. The capacitor discharges into the output circuit for the duration of the C-1 pulse, during which time an analog to digital conversion is made, at the end of which switches S-3a and S-3b return to their initial position, and the end of the C-1 clock pulse simultaneously reverses the "PHASE" pulse to the negative, so that the next pulse received from capacitor C-1 will be inverted at the S-2a and S-2b switches, to be passed through the amplifying and measuring circuits and re-inverted at S-2c and S-2d so that the output circuit receives the inverted signal uninverted.

The sequencing of FIG. 6 may only last for two phase cycles, resulting in two pulse measurements of opposite polarity. However, depending on the type of usage, the pulses and the measuring could go on for perhaps 100 pulse pairs. If the apparatus is used to make many closely spaced measurements, for example 50 in a second, in a small region of ocean water to detect small currents and salinity gradients, the apparatus could make 50 separate inverted pulse pair measurements in a second.

On the other hand, if major regional measurements of the oceans are being made, one measurement consisting of 100 averaged pulse pairs may be made at one location.

With continued reference to FIG. 7, a calibration voltage circuit 46 is included for a fine offset voltage adjustment of amplifier A-4. The other features in the schematic of FIG. 7 are standard, comprising resisters and capacitors, a voltage source, switches and amplifiers.

Source 26 is illustrated in more detail in FIG. 7 at the lower right. A battery maintains a charge on capacitor C-3 and C-4 when switch S-4 is in its normal state. Switch S-4 is a quadruple pole, double throw switch controlled by the "MEAS" wave form. The source 26 has the purpose and effect of removing the circuitry from ground and isolating it from the source battery.

When the "MEAS" pulse switches all the polls at S-4, which occurs during the positive cycle of the "MEAS" pulse diagram of FIG. 6, both positive and negative source voltage is made available to all of the amplifiers in the circuit. During the time when the circuit is not in use, and during the time when the pulse just delivered is being processed by the amplifiers, there is no drain on the battery, so that the source circuit 26 has the second function of extending battery life by disconnecting the battery from the circuit (actually, disconnecting the capacitors C-3 and C-4 from the circuit) when the battery is not needed.

The instrument described and claimed herein has been in operation for a number of months, and has become known for its portability, accuracy and its ability to consistently repeat measurements. It constitutes a significant contribution to oceanography, which is in keeping with the increased interest in exploring the oceans, and the heightened level of technology and precision largely engendered by the computer revolution with which ongoing research is being conducted.

I claim:

1. An electrolyte conductivity measuring apparatus comprising:
   (a) a probe for a least partial immersion in an electrolyte, said probe comprising:
      (i) a substantially planar insulating substrate strip;
      (ii) a first pair of electrodes on respective opposite planar sides of said substrate strip adjacent one end thereof;
      (iii) an insulating sheath surrounding said one end of said strip and being bonded to the edges thereof and extending beyond said one end to define a current flow region between said first pair of electrodes around said one end;
   (b) a current source connected said electrodes and a circuit for producing a current between said electrodes;
   (c) means for gaging the current produced by said source between said first pair of electrodes and outputting the measurement of said current; and,
   (d) a second pair of electrodes, each being mounted on an opposite side of said substrate strip, respectively spaced from said first pair of electrodes and connected to said current source to provide voltage level feedback information in said circuit.

2. Structure according to claim 1 wherein said second pair of electrodes are on the opposite side of the respective ones of said first pair of electrodes from said one end of said substrate.

3. Structure according to claim 2 wherein said electrodes comprise metallic deposits on said substrate and have exposed tips adjacent said one end of said substrate strip and are otherwise covered with a layer of insulating material over both sides of said strip.

4. Structure according to claim 3 wherein said electrodes comprise metallic deposits of a composition of platinum.

5. Structure according to claim 1 wherein the distance between the tips of said electrodes and said one end of said substrate strip is less than the distance between said tips and the end of said sheath on the other side of said tips from said one end of said strip, so that the current path between the electrodes of said first pair is much shorter around said one end of said substrate strip than in the other direction.

6. An electrolyte conductivity measuring apparatus comprising;
   (a) a probe immersible in an electrolyte to be measured, said probe at least partially defining a current flow region through said electrolyte and having a first pair of current electrodes spanning a distance in said current flow region, and a second pair of voltage electrodes disposed in said current region for measuring the potential difference therebetween;
   (b) a voltage source for generating an accurately determined source voltage;
   (c) a first amplifier circuit for applying voltage from said voltage source across said current electrodes, thereby causing a current to flow therebetween;
   (d) said first amplifier circuit receiving input from said voltage electrodes and having feedback means for stabilizing the voltage across said voltage electrodes at a predetermined level by adjusting the current between said current electrodes utilizing a dropping resister in series with said current electrodes for dropping voltage in proportion to the current between said current electrodes;
   (e) a second amplifier circuit for amplifying the voltage across said voltage dropping resister and outputting a signal to an external signal register and processing means;
   (f) a first polarity reversing means and control means for alternately reversing the polarity of the signal from said voltage source to said first amplifier circuit such that consecutive pulses to said first amplifier circuit are of opposite polarity;
   (g) a second polarity reversing means operatively connected to said second amplifier circuit and control means to reverse the polarity of the pulse output from said second amplifier circuit for alternate pulses such that only pulses of the same polarity are out-putted to said signal register and processing means; and,
   (h) including control means which space said consecutive pulses to said first amplifier circuit for a time at least equal to the duration of each pulse, thus preventing the polarization and deterioration of said electrodes.

7. An electrolyte conductivity measuring apparatus comprising;
   (a) a probe immersible in an electrolyte to be measured, said probe at least partially defining a current flow region through said electrolyte and having a first pair of current electrodes spanning a distance in said current flow region, and a second pair of voltage electrodes disposed in said current region for measuring the potential difference therebetween;
   (b) a voltage source for generating an accurately determined source voltage;
   (c) a first amplifier circuit for applying voltage from said voltage source across said current electrodes, thereby causing a current to flow therebetween;
   (d) said first amplifier circuit receiving input from said voltage electrodes and having current regulating feedback means for stabilizing the voltage across said voltage electrodes at a predetermined level by adjusting the current between said current electrodes utilizing a voltage dropping resister in series with said current electrodes for dropping voltage in proportion to the current between said current electrodes;
   (e) a second amplifier circuit for amplifying the voltage across said voltage dropping resister and outputting a signal to an external signal register and processing means; and,
   (f) whereby said amplifier circuits are battery powered and are electrically isolated from the battery by a capacitive charge transfer system which includes a capacitor which is alternately switched by said capacitive charge system from connection to the battery and power supply during a charge cycle, to connection to said amplifier circuits isolated from said battery.

* * * * *